US005480783A

United States Patent [19]

Haff

[11] Patent Number: 5,480,783

[45] Date of Patent: Jan. 2, 1996

[54] METHOD FOR REDUCING BACKGROUND SIGNALS IN DNA REPLICATION/DETECTION ASSAYS

[75] Inventor: Lawrence A. Haff, Wilton, Conn.

[73] Assignee: The Perkin-Elmer Corporation, Norwalk, Conn.

[21] Appl. No.: 221,163

[22] Filed: Mar. 31, 1994

[51] Int. Cl.[6] .............................. C12P 19/34; C12Q 1/68; C07H 21/04; C12N 15/00

[52] U.S. Cl. ............................ 435/91.2; 435/6; 435/183; 435/91.1; 536/23.1; 536/24.33; 536/25.3; 935/16; 935/76; 935/77; 935/78

[58] Field of Search ............................ 435/6, 91.1, 91.2, 435/183; 536/24.33, 23.1, 25.3; 935/76–78, 16

[56] References Cited

U.S. PATENT DOCUMENTS

| | | | |
|---|---|---|---|
| 5,035,996 | 7/1991 | Hartley | 435/6 |
| 5,075,216 | 12/1991 | Innis et al. | 435/6 |
| 5,108,892 | 4/1992 | Burke et al. | 435/6 |
| 5,232,829 | 8/1993 | Longiaru et al. | 435/6 |

OTHER PUBLICATIONS

Long, A. A. et al., Histochemistry, vol. 99, 151–162 (1993).

Sallstrom, J. A. et al., Anticancer Research, vol. 13, 1153 (1993).

Nuovo, G. J. et al., American Journal of Pathology, vol. 139, No. 6, 1239–1244 (1991).

Paabo, S., Proc. Natl. Acad. Sci. USA, vol. 86, 1939–1943 (1989).

Gosden, J. et al., Biotechniques, vol. 15 No. 1, 78–80 (1993).

Chou, Q. et al., Nucleic Acid Research, vol. 20 No. 7, 1717–1723 (1992).

Hofler, H., Histochemistry, 1103–1104 (1993).

Komminoth, P. et al., Diagnostic Molecular Pathology, vol. 1 No. 2, 85–97 (1992).

Sanger et al., *PNAS, USA*, vol. 74, No. 12, pp. 5463–5467, Dec. 1977.

*Primary Examiner*—W. Gary Jones

*Assistant Examiner*—Bradley L. Sisson

*Attorney, Agent, or Firm*—Edwin T. Grimes; George W. Rauchfuss, Jr.

[57] ABSTRACT

A kit and method for reduction of primer-independent background signals in a DNA replication/detection assay, particularly in a direct in situ PCR amplification/detection assay, for a target DNA sequence in DNA sample, comprising pretreating the DNA sample, containing the target DNA sequence to be replicated/amplified and assayed, with DNA polymerase and one or more dideoxynucleoside triphosphates prior to conducting the replication/amplification steps.

31 Claims, No Drawings

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
( A ) LENGTH: 22 bases
( B ) TYPE: nucleic acid
( C ) STRANDEDNESS: single
( D ) TOPOLOGY: linear ( i i ) MOLECULE TYPE: Other nucleic acid ( x i ) SEQUENCE DESCRIPTION: SEQ ID NO: 1:

CATTTCCACG TCAACAGAAT TG 22

( 2 ) INFORMATION FOR SEQ ID NO: 2:

-continued ( i ) SEQUENCE CHARACTERISTICS:
( A ) LENGTH: 22 bases
( B ) TYPE: nucleic acid
( C ) STRANDEDNESS: single
( D ) TOPOLOGY: linear ( i i ) MOLECULE TYPE: Other nucleic acid ( x i ) SEQUENCE DESCRIPTION: SEQ ID NO: 2:

AGCACAGGAT TGGATATTCC AT 22

METHOD FOR REDUCING BACKGROUND SIGNALS IN DNA REPLICATION/DETECTION ASSAYS

FIELD OF THE INVENTION

The invention of this application relates to a kit and a method for reducing primer-independent background signals in a DNA replication/detection assay, particularly in a direct in situ PCR amplification/detection assay. More particularly, the invention relates to a kit and a method for reducing or substantially eliminating primer-independent background signals produced when DNA in paraffinized tissue or cell cultures is amplified in a direct in situ PCR amplification/detection assay.

BACKGROUND OF THE INVENTION

Diagnostic assays for detecting pathogens or other targets have employed labeled DNA probes which are added to DNA samples and permitted to hybridize to the fixed DNA sample. Hybridization indicates the presence of the pathogen or other target. An increase in sensitivity of the assay can be obtained by amplification of the DNA sample.

Relatively recently, a significant improvement in DNA amplification has been provided. Known as the polymerase chain reaction (PCR) technique, it may be generally described in the following manner. The technique is an enzymatic, in vitro synthesis method for replicating or amplifying specific target DNA sequences in DNA samples. The technique employs DNA polymerase, deoxynucleoside triphosphates and two oligonucleotide primers that hybridize to opposite strands of the DNA sample and flank the region of interest in the target DNA sequence. Exponential amplification of the target sequence is obtained by a repetitive series of steps comprising template denaturation, primer annealing and extension of the annealed primers by DNA polymerase, generally referred to as thermal cycling steps. Such a PCR technique is capable of producing amplification of the target sequence, which termini are defined by the 5'-ends of the oligonucleotide primers employed, by a factor of up to about $10^9$. The PCR technique is disclosed, for example, in U.S. Pat. Nos. 4,683,195; 4,683,202; 4,800,159 and 4,965,188.

In situ PCR is a relatively new variant of the standard PCR technique. In in situ PCR, the DNA sample is typically a slice of fixed tissue with morphologically recognizable cells. The PCR amplification products remain at, and can be detected at, their site of origin indicating which cells contain the target DNA sequence.

Once a DNA sample is physically amplified in a PCR amplification procedure, detection of the presence or absence of the desired target gene sequence can be accomplished by a variety of isotopic or non-isotopic detection methods. One of the most desirable and preferred methods to detect such PCR target sequence is to amplify the DNA sample in the presence of a labeled molecule, such as a labeled oligonucleotide primer or labeled deoxynucleotide, which becomes incorporated into the amplified DNA. This is generally referred to as direct in situ PCR detection. In general, the labeled molecules are incorporated into nucleotide analogues of dATP, dCTP, dGTP, dTTP or dUTP and are incorporated directly into the PCR amplification products. The labels are generally small molecules like biotin, horseradish peroxidase, digoxigenin, $^{32}$P and the like. PCR amplification products containing these labels can be detected directly, or with enzymes coupled to antibodies to the label. The enzymes can generate any of many different reporter molecules, such as for example, isotopic, fluorescent or colorimetric reporter molecules.

One of the major advantages of direct in situ PCR detection is that many labels can be incorporated into the amplification products at many different sites, particularly if one employs a labeled nucleotide. This generally increases the signal generated and thus lowers the detection limit. A further advantage of direct in situ PCR is that the detection procedure is greatly simplified, since no DNA probes, DNA hybridization or washing steps are required.

Alternatively, unlabeled PCR amplification products can be detected indirectly with a DNA or RNA probe that itself contains a label. This procedure has been variously termed in situ PCR hybridization, indirect PCR detection, or probe-based PCR detection. This method has the disadvantage of requiring several additional steps. Much less signal is also produced, so the detection limit is often adversely impacted. This method, however, provides for better specificity than direct in situ PCR since most nonspecific amplification products will not hybridize to the probe.

Thus, it will be appreciated that there is much to recommend in the direct in situ PCR detection procedure and it would be the procedure of choice in many instances. However, a major limitation to direct in situ PCR detection is that nonspecific PCR amplification products are indistinguishable from specific amplification products. If large amounts of nonspecific products are produced, a false positive may be produced. The production of nonspecific products, even if in reproducible amounts, also raises the background level and therefore negatively impacts the minimum detection level. The quality of results obtained using direct in situ PCR detection is dependent upon the quality of the PCR amplification reaction itself. In contrast, probe-based PCR detection is much less sensitive to the presence of nonspecific products.

Since the discovery of the PCR technique, a number of factors have been identified in solution-phase PCR which impact upon the specificity of the PCR amplification reaction. Among those factors are the following sources of nonspecificity problems: non-optimized PCR protocol, primer nonspecificity, primer oligomerization and primer-independent nonspecificity. The solution to the problem due to non-optimized PCR protocol is to optimize the PCR protocol and thermal cycling parameters. A solution to the problem of primer nonspecificity is the selection of a primer of a different nucleotide sequence. Another solution to the problem of primer nonspecificity, as well as the problem of primer oligomerization, is the so-called hot-start technique disclosed by Chou et al. NucleicAcidResearch, Vol. 20, No. 7 1717–1723 (1992). In this technique, the entire PCR reaction mixture is kept relatively warm at all times once constituted but prior to thermal cycling. This prevents nonspecific primer annealing and extension which could otherwise occur at lower temperatures. The hot-start technique has been demonstrated to be of great value with in situ PCR in lowering nonspecific signal due to primer nonspecificity and primer oligomerization, see Nuovo et al., Amer. Journal of Pathology, Vol. 139, No. 6, 1239–1244 (Dec. 1991).

However, the fourth source of nonspecific signal identified hereinbefore, namely primer-independent nonspecific amplification, is a phenomenon observed in the absence of primers and is not curable by the hot-start technique. This problem of primer-independent nonspecificity has been observed by various investigators who have concluded that the problem is so severe that direct detection of amplified target sequence in situ PCR could not be considered a suitable technique.

While the problem of primer-independent nonspecificity has been illustrated hereinbefore with respect to in situ PCR amplification where it is a particularly bothersome problem, it will be appreciated that such primer-independent nonspecificity can also be a problem in other DNA replication procedures, such a solution-phase PCR amplification or in the primed in situ extension (PRINS) replication technique which uses only a single oligonucleotide primer, which is annealed to chromosomal DNA and extended in situ with the incorporation of labeled oligonucleotides. In the various DNA replication/amplification procedures, the production of primer-independent nonspecific products presents a serious problem in the detection phase of an assay procedure since the nonspecific products can significantly raise the background level to such high levels that false positives are produced and also negatively impact the minimum or lower detection level of the assay.

It is therefore an object of this invention to provide a procedure for reducing or substantially eliminating production of primer-independent nonspecific products during a process for replicating or amplifying and detecting a target DNA sequence in a DNA sample subjected to a DNA replication/amplification process. A further object of this invention is to provide a procedure for reducing or substantially eliminating production of primer-independent nonspecific products during a PCR amplification process, particularly in an in situ PCR amplification process and more particularly in a direct in situ PCR amplification and detection process.

BRIEF SUMMARY OF THE INVENTION

The present invention provides a kit and a procedure for reducing or substantially eliminating primer-independent nonspecific background produced by the production of primer-independent nonspecific products during processes for replicating or amplifying and detecting a target DNA sequence in a DNA sample by DNA replication or amplification processes in which:

(a) the target DNA sequence is replicated by a process using deoxynucleoside triphosphates and one or more oligonucleotide primers that hybridize to at least one strand in the target sequence of the DNA sample and detection of the target sequence follows replication, or (b) the target DNA sequence is amplified by a PCR amplification process by thermal cycling between annealing/extension and denaturing steps using oligonucleotide primers that hybridize to opposite strands of a DNA sample and flank the target DNA sequence and detection of the target sequence follows amplification, or (c) the target DNA sequence is amplified by a direct in situ PCR amplification and detection process by providing to the DNA sample: DNA polymerase, each of four deoxynucleoside triphosphates and a set of oligonucleotide primers that hybridize to opposite strands of the DNA sample and flank the target sequence, wherein at least one of the four deoxynucleoside triphosphate is labeled, and amplifying the target DNA sequence by thermal cycling said components under conditions which permit a repetitive series of PCR cycling steps of: denaturing the DNA sample into opposite strands, annealing the primers to the denatured strands and extending the annealed primers by DNA polymerase exponentially amplifying the target DNA sequence creating labeled targeted DNA sequences, said procedure for reducing or substantially eliminating primer-independent nonspecific products and background comprising subjecting the DNA sample to a pre-treatment prior to the replication/amplification process, wherein said pre-treatment comprises contacting the DNA sample with at least one dideoxynucleoside triphosphate and a DNA polymerase for a time and at a temperature sufficiently to covalently bond a dideoxynucleoside to 3'-terminal ends in the DNA sample, and then separating the treated DNA sample from the dideoxynucleoside triphosphate and the DNA polymerase, prior to the replication/amplification process.

DETAILED DESCRIPTION OF THE INVENTION

In studying the problem of primer-independent nonspecificity it was noticed that high primer-independent nonspecific background was routinely observed when paraffinized tissues were employed as the DNA sample, but not in cell suspensions, which are not subject to paraffinization. Additionally, such high primer-independent nonspecific background was not observed in frozen tissue sections, which are also not subject to paraffinization but are subjected to most of the other tissue preparation steps, such as, sectioning and mounting, formalin fixation and protease digestion steps. Sometimes, high PCR background were observed with cell suspensions, but this could always be blocked with the aforementioned hot start technique or by withholding primers. This indicates that the background problem in cell suspensions was primer nonspecificity, not primer-independent nonspecificity.

This evidence led to the belief that one of the steps involved in the paraffinization or deparaffinization procedure was responsible for the primer-independent nonspecific background problem. It was also discovered that if the paraffinization step was omitted, elevated temperature alone was sufficient to create primer-independent nonspecific background. This was observed when tissue sections of vulvar and tonsilar biopsies were placed on silane slides and fixed for 4 to 15 hours in 10% buffered formalin and sections from each tissue were heated in a dry oven at 65° C. for 4 hours. A primer-independent signal was evident at optional protease digestion time for each tissue after this heating step. However, if the tissue is not heated to 65° C., it does not exhibit primer-independent nonspecific PCR background. The presence of nonspecific signal in the absence of primers suggests that DNA polymerase mediated repair of DNA gaps may be occurring.

Other control experiments demonstrated that the problem clearly originated from the DNA in the samples. RNA-based in situ PCR did not demonstrate any background problems. The background also did not appear if the sample's DNA were eliminated by prior deoxyribonuclease treatment. It also disappeared if the samples were subjected to extended protease treatment. Cells, as opposed to tissues, are generally not paraffinized and this background problem is generally not observed with cells. However, sometimes it is desirable to treat cells as a tissue. If paraffinized, these paraffinized cells exhibit primer-independent nonspecific background.

Having discovered that the primer-independent background problem was caused by subjecting DNA samples to elevated temperatures, it was discovered that pre-treatment of the DNA sample with a dideoxynucleoside triphosphate and a DNA polymerase and thereafter separating the treated DNA sample from dideoxynucleoside triphosphate and DNA polymerase prior to the PCR amplification process substantially eliminated or reduced the observed primer-independent nonspecific background problem.

While not being bound by the following explanation, it is believed that the primer-independent nonspecific background problem and its unobvious solution may be explained by the following. It is believed that the cause of the aforediscussed primer-independent nonspecific background problems involves the scission of one strand of the double-stranded DNA samples, creating many single-stranded breaks in the DNA sequence, which breaks have 3'-end hydroxyl terminal nucleotides which serve as polymerization initiation sites for the DNA polymerase and deoxynucleoside triphosphates during the PCR amplification process. Addition of a 2'3'-dideoxynucleotide, from the corresponding triphosphate, to the 3'-terminal end of a DNA strand at the break is believed to prevent its later extension during the PCR amplification process.

While it has been observed that the background problem due to primer-independent nonspecificity solved by this invention is particularly present when employing a DNA sample that has been fixed, paraffinized and deparaffinized, the solution is also applicable to such background problem that arises when employing a DNA sample that has been subjected to an elevated temperature of at least about 37° C., and more particularly to a DNA sample that has been subjected to an elevated temperature of from about 45° to about 65° C., preferably 50° C. or more, for a period of from about 10 minutes to about 16 hours.

Also, the solution to the problem of primer-independent nonspecific background has applicability not only in direct in situ PCR amplification but also in various PCR amplification processes as well as in other DNA replication processes, such as in a PRINS replication process where primer-independent nonspecificity background is a problem.

In the pre-treatment process of this invention the DNA sample to be subjected to replication or amplification is contacted with at least one dideoxynucleoside triphosphate and a DNA polymerase for a time and at a temperature sufficient to covalently bond a dideoxynucleoside to 3'-terminal ends in the DNA sample. Although the temperature may be as low as about 20° C., it is preferably a temperature of at least about 37° C. to about 72° C. for a period of at least about one minute or more, more preferably for a period of from about 1 to about 15 minutes or more at a temperature of about 55° C. or more. In a further embodiment of this invention the DNA sample may be treated with dideoxynucleoside triphosphate and DNA polymerase in a thermal cycling operation wherein these components are contacted during thermal cycling between two stages. Preferably, the thermal cycling stages of this pre-treatment procedure comprise a first stage at a temperature of from about 37° C. to about 72° C. for a period of about 10 seconds to about 1 minute and a second stage at a temperature of from about 80° C. to about 105° C., preferably about 94° C., for a period of time of from about 10 seconds to about 1 minute. Generally from about 1 to about 10 cycles between these two stages will be employed when such a thermal cycling sequence is employed in the pre-treatment process.

While the pre-treatment process of this invention may be employed using a single dideoxynucleoside triphosphate, such as ddTTP, if desired one can employ two or more dideoxynucleoside triphosphates, such as ddATP, ddGTP, ddCTP as well as ddTTP. When a single dideoxynucleoside triphosphate is employed in the pre-treatment process of this invention, the reaction mixture will also contain the other three deoxynucleotides so that the gaps in the site of the scissions will be filled in until a position is reached whereby the dideoxynucleotide adds to the 3'-terminal ends of the scissions. If two or more dideoxynucleosides are employed in the pre-treatment process of this invention, the reaction mixture should also employ the other deoxynucleotides not present as dideoxynucleotides. If desired, the reaction mixture can always contain all four deoxynucleotides as was the case in the following examples.

A kit for the use in said pre-treatment comprises at least one dideoxynucleoside triphosphate and DNA polymerase. The kit can comprise two or more dideoxynucleoside triphosphates. Such a kit preferably comprises dideoxythymidine triphosphate and Taq DNA polymerase. The kit can additionally comprise the four deoxynucleoside triphosphates dATP, dCPT, dGPT, dTTP.

The pre-treatment process of this invention may employ any suitable DNA polymerase such as, for example, Taq polymerase and the like. The DNA polymerase chosen for use in any pretreatment procedure of this invention will generally be chosen to incorporate the greatest amount of dideoxynucleoside triphosphate(s) at the lowest concentration of dideoxynucleoside triphosphate(s) in the least time. The optimal DNA polymerase would also preferably lack any exonuclease activity to avoid creating or extending any single-stranded breaks in the DNA sample. As an example of such a DNA polymerase there may be mentioned AmpliTaq® DNA polymerase, Stoffel fragment (available from Perkin-Elmer Corporation as product No. N808-0038).

After reacting the DNA sample with the dideoxynucleoside triphosphate in the presence of DNA polymerase, for a time and at a temperature sufficient to covalently bond a dideoxynucleoside to 3'-terminal ends in the DNA sample, the treated DNA is separated from dideoxynucleoside triphosphate and DNA polymerase. Any suitable separation technique may be employed. For example, when employing a fixed DNA sample for in situ PCR amplification, the treated sample may be separated by washing. However, for other amplification processes such as solution PCR, it will be necessary to precipitate the DNA sample by a suitable desalting process or separate the DNA sample by any other suitable separation procedure, such as for example, by precipitation with alcohol or by various chromatographic processes such as ion exchange, reversed phase and size exclusion chromatography.

The DNA sample may be from any suitable biological sample, such as all cells, for example, plant, animal, bacterial, fungal and microbial cells, as well as from viruses and chromosomal spreads.

The invention is illustrated but not limited by the following examples. In the examples the following procedures were employed for sample preparation, amplification and detection of bcl-2 gene.

TISSUE PREPARATION

Four μM sections of paraffin embedded liver, vulvar, tonsilar, and lymph node tissues were placed on silane coated glass slides. Tissue samples were fixed in 10% neutral buffered formalin for either 6 hours or 8 hours. Protease digestion was done using pepsin at 2 mg/ml in 0.01 N HC1 at room temperature. Three serial sections were placed on each slide so that adjustments to a given variable could be compared under identical reaction conditions.

Sections were deparaffinized in xylene for minutes, washed in 100% ethanol for 5 minutes, then air dried.

IN SITU PCR

After deparaffinization and optimal protease digestion for 15 minutes, the following reaction mixture (25μl) was added to each slide: 2.5μl PCR buffer II (GeneAmp® kit, Perkin-Elmer Corporation), 4.5μl $MgCl_2$ (25 mM stock solution), 4.0 μl dNTP solution (stock solution 800μM), 1.0μl 2% bovine serum albumin, 0.4μl digoxigenin dUTP solution (1μM stock solution) +/−1μl of hereinafter identified bcl-2 primer 1 (SEQ ID No: 1) and bcl-2 primer 2 (SEQ ID No: 2) (each stock 20 μM) for bcl-2 gene + 11 μl (or 13μl if the primers were omitted) of water, 0.6μl of Taq polymerase. The solution was added to the slide, covered with one large polypropylene coverslip anchored with 2 small drops of nail polish, and placed in an aluminum foil "boat". This was placed on the aluminum block of the thermal cycler which was ramped to 80° C. At this temperature, the coverslip was overlaid with 1 ml of heated mineral oil. The DNA was denatured at 94° C. for 3 minutes, followed by 20 cycles at 55° C. for 2 minutes and 94° C. for 1 minute. After removal of the coverslip, sequential 5 minutes washes in xylene and 100% ethanol were done, and the slides air-dried. Detection of digoxigenin incorporated into the PCR product was done with alkaline phosphatase-conjugated antidigoxigenin-labeled antibody at a 1:50 dilution. The alkaline phosphatase-based colorimetric detection method used the chromogen nitroblue tetrazolium (NBT) which, in the presence of 5-bromo-4-chloro-3-indolylphosphate (BCIP), yields a purple-blue precipitate as the marker for positive cells. The counterstain, nuclear fast red, stains nuclei and cytoplasm pale pink. Tests were done in triplicate and the scoring system for the signal was as follows: 0, 1+=<25% of cells positive, 2+=25–50% cells positive, and 3+=>50% of cells positive. The primers employed are:

bcl–2 primer 1 SEQ ID NO: 1 5'-CATTTCCACGTCAACAGAATTG-3' bcl–2 primer 2 SEQ ID NO: 2 5'-AGCACAGGATTGGATATTCCAT-3'.

The examples of in situ PCR amplification were conducted without first conducting the pre-treatment with dideoxynucleoside triphosphate and DNA polymerase (Examples 1 and 2) and then the same PCR amplification examples were repeated after first conducting a dideoxynucleoside triphosphate pretreatment according to this invention (Examples 3 and 4). The dideoxynucleoside triphosphate pre-treatment in the examples was conducted in the following manner. After protease digestion of the tissue sections and prior to in situ PCR amplification thereof, the tissue sections were pre-treated by incubation in a solution which contained 2.5μl PCR buffer II (Gene Amp Kit), 4.5μl $MgCl_2$ (25 mM stock solution), 4.0μl dNTP solution (stock solution 800 μM, i.e. 200 μM each of the four deoxynucleotides), 2.5μl of dideoxythymidine triphosphate (1,000 μM stock solution), 1.0μl 2% bovine serum albumin, +9.7μl of water, 0.8μl of Taq polymerase (5 units/μl) for 30 minutes at 55° C. The treated tissue samples were then separated from dideoxythymidine triphosphate and Taq polymerase by washing with distilled water. Thereafter, PCR amplification and detection of the pre-treated tissue samples was performed in a manner identical to that described hereinbefore but in the absence of any primers. The results of the foregoing examples are set forth in the following Table.

TABLE

| Example No. | Fixation Time | Dideoxy Pre-treatment | Primer-Independent Signal |
|---|---|---|---|
| Example 1 | 6 hrs | No | 3+ |
| Example 2 | 8 hrs | No | 3+ |
| Example 3 | 6 hrs | Yes | 0 |
| Example 4 | 8 hrs | Yes | 0 |

From the data in the above Table it is evident that the dideoxy pre-treatment eliminated (0 value) the primer-independent nonspecific signal that had been produced (3+ value) without the dideoxy pre-treatment.

With the foregoing description of the invention, those skilled in the art will appreciate that modifications may be made to the invention without departing from the spirit thereof. Therefore, it is not intended that the scope of the invention be limited to the specific embodiments illustrated and described.

I claim:

1. In a method for replication and detection of a target DNA sequence in a DNA sample by a replication process using deoxynucleoside triphosphates and one or more oligonucleotide primers that hybridize to at least one strand in the target sequence of the DNA sample and detecting said target sequence following replication, the improvement comprising reducing primer-independent nonspecific background by subjecting the DNA sample to a treatment prior to the replication process, said treatment comprising:

(a) contacting the DNA sample with at least one dideoxynucleoside triphosphate and a DNA polymerase at a temperature and time sufficient to covalently bond a dideoxynucleoside to 3'-terminal ends in the DNA sample, and (b) separating the treated DNA sample from dideoxynucleoside triphosphate and DNA polymerase.

2. In a method for amplification and detection of a target DNA sequence in a double-stranded DNA sample by a polymerase chain reaction (PCR) amplification process by thermal cycling between annealing/extension and denaturing steps using oligonucleotide primers that hybridize to opposite strands of the DNA sample and flank the target DNA sequence and detection of said target sequence following amplification, the improvement comprising reducing primer-independent nonspecific background by subjecting the DNA sample to a treatment prior to the PCR amplification process, said treatment comprising:

(a) contacting the DNA sample with at least one dideoxynucleoside triphosphate and a DNA polymerase at a temperature and time sufficient to covalently bond a dideoxynucleoside to 3'-terminal ends in the DNA sample, and (b) separating the treated DNA sample from dideoxynucleoside triphosphate and DNA polymerase.

3. A method according to claim 2 wherein the PCR amplification process is an in situ PCR process utilizing a labeled deoxynucleoside triphosphate and separation of the treated DNA sample from dideoxynucleoside triphosphate and DNA polymerase occurs by washing.

4. A method according to claim 2 wherein the DNA sample resides in a tissue or cell culture that has been subjected to an elevated temperature of above about 37° C.

5. A method according to claim 3 wherein the DNA sample resides in a tissue or cell culture that has been subjected to an elevated temperature of above about 37° C.

6. A method according to claim 4 wherein the DNA sample to be treated prior to the PCR amplification process resides in a DNA sample that has been fixed, paraffinized and deparaffinized.

7. A method according to claim 5 wherein the DNA sample to be treated prior to the PCR amplification process resides in a DNA sample that has been fixed, paraffinized and deparaffinized.

8. A method according to claim 2 wherein the DNA sample is treated with the dideoxynucleoside triphosphate and DNA polymerase at a temperature of at least about 37° C. for a period of at least about one minute.

9. A method according to claim 5 wherein the DNA sample is treated with the dideoxynucleoside triphosphate and DNA polymerase at a temperature of at least about 37° C. for a period of at least about one minute.

10. A method according to claim 7 wherein the DNA sample is treated with the dideoxynucleoside triphosphate and DNA polymerase at a temperature of at least about 37° C. for a period of at least one minute.

11. A method according to claim 2 wherein the contacting of the DNA sample with the dideoxynucleoside triphosphate and DNA polymerase occurs during thermal cycling between two stages comprising:

(a) a first stage at a temperature of from about 37° C. to about 72° C. for a period of time of from about 10 seconds to about 1 minute;

(b) a second stage at a temperature of from about 80° C. to about 105° C. for a period of time of from about 10 seconds to about 1 minute.

12. A method according to claim 5 wherein the contacting of the DNA sample with the dideoxynucleoside triphosphate and DNA polymerase occurs during thermal cycling between two stages comprising:

(a) a first stage at a temperature of from about 37° C. to about 72° C. for a period of time of from about 10 seconds to about 1 minute;

(b) a second stage at a temperature of from about 80° C. to about 105° C. for a period of time of from about 10 seconds to about 1 minute.

13. A method according to claim 7 wherein the contacting of the DNA sample with the dideoxynucleoside triphosphate and DNA polymerase occurs during thermal cycling between two stages comprising:

(a) a first stage at a temperature of from about 37° C. to about 72° C. for a period of time of from about 10 seconds to about 1 minute;

(b) a second stage at a temperature of from about 80° C. to about 105° C. for a period of time of from about 10 seconds to about 1 minute.

14. A method according to claim 2 wherein the DNA sample is contacted with two or more dideoxynucleoside triphosphates.

15. A method according to claim 5 wherein the DNA sample is contacted with two or more dideoxynucleoside triphosphates.

16. A method according to claim 2 wherein the DNA sample is contacted with dideoxythymidine triphosphate, Taq DNA polymerase, deoxyadenosine triphosphate, deoxycytidine triphosphate and deoxyguanosine triphosphate.

17. A method according to claim 5 wherein the DNA sample is contacted with dideoxythymidine triphosphate, Taq DNA polymerase, deoxyadenosine triphosphate, deoxycytidine triphosphate and deoxyguanosine triphosphate.

18. A method according to claim 8 wherein the DNA sample is treated with the DNA polymerase and dideoxynucleoside triphosphate at a temperature of from about 37° C. to about 72° C. for a period of from about 1 to about 15 minutes.

19. A method for amplification and detection of a target DNA sequence in a DNA sample by polymerase chain reaction (PCR) enzymatic synthesis of said target DNA sequence, said method comprising:

(a) providing a double-stranded DNA sample and treating said DNA sample by contacting said DNA sample with at least one dideoxynucleoside triphosphate and a DNA polymerase at a temperature and time sufficient to covalently bond a dideoxynucleoside to 3'-terminal ends in the DNA sample, (b) separating said treated DNA sample from dideoxynucleoside triphosphate and DNA polymerase, and thereafter (c) providing to the separated, treated DNA sample: DNA polymerase, each of four deoxynucleoside triphosphates and a set of oligonucleotide primers that hybridize to opposite strands of the DNA sample and flank the target sequence, wherein at least one of said four deoxynucleoside triphosphates is labeled, (d) amplifying the target DNA sequence employing the DNA polymerase and four deoxynucleoside triphosphates under conditions which permit a repetitive series of PCR cycling steps of: denaturating of the DNA sample into opposite strands, annealing of the primers to the denatured strands and extending the annealed primers by DNA polymerase·exponentially amplifying the target DNA sequence creating labeled target DNA sequences, and (e) detecting and/or measuring the labeled target DNA sequences to determine the presence or absence of the target DNA sequence in the DNA sample.

20. A method according to claim 19 wherein the PCR amplification process is an in situ process utilizing a labeled deoxynucleoside triphosphate and separation of the treated DNA sample from dideoxynucleoside triphosphate and DNA polymerase occurs by washing.

21. A method according to claim 20 wherein the DNA sample resides in a tissue or cell culture that has been subjected to an elevated temperature of above about 37° C.

22. A method according to claim 21 wherein the DNA sample to be treated prior to the PCR amplification process resides in a DNA sample that has been fixed, paraffinized and deparaffinized.

23. A method according to claim 19 wherein the DNA sample is contacted with two or more dideoxynucleosides triphosphates.

24. A method according to claim 22 wherein the DNA sample is contacted with two or more dideoxynucleoside triphosphates.

25. A method according to claim 19 wherein the DNA sample is contacted with dideoxythymidine triphosphate, Taq DNA polymerase, deoxyadenosine triphosphate, deoxycytidine triphosphate, deoxythymidine triphosphate and deoxyguanosine triphosphate.

26. A method according to claim 22 wherein the DNA sample is contacted with dideoxythymidine triphosphate, Taq DNA polymerase, deoxyadenosine triphosphate, deoxycytidine triphosphate, deoxythymidine triphosphate and deoxyguanosine triphosphate.

27. A method according to claim 19 wherein the DNA sample is treated with the DNA polymerase and dideoxynucleoside triphosphate at a temperature of from about 37° C. to 72° C. for a period of from about 1 to 15 minutes.

28. A method according to claim 22 wherein the DNA sample is treated with the DNA polymerase and dideoxynucleoside triphosphate at a temperature of from about 37° C. to 72° C. for a period of from about 1 to 15 minutes.

29. A method according to claim 19 wherein the contacting of the DNA sample with the dideoxynucleoside triphosphate and DNA polymerase occurs during thermal cycling between two stages comprising:

(a) a first stage at a temperature of about 37° C. to about 72° C. for a period of time of from about 10 seconds to about 1 minute;

(b) a second stage at a temperature of from about 80° C. to about 105° C. for a period of time of from about 10 seconds to about 1 minute.

30. A method according to claim 22 wherein the contacting of the DNA sample with the dideoxynucleoside triphosphate and DNA polymerase occurs during thermal cycling between two stages comprising:

(a) a first stage at a temperature of from about 37° C. to about 72° C. for a period of time of from about 10 seconds to about 1 minute;

(b) a second stage at a temperature of from about 80° C. to about 105° C. for a period of time of from about 10 seconds to about 1 minute.

31. A deoxynucleoside triphosphate-free mixture consisting essentially of a DNA polymerasc and the four dideoxynucleoside triphosphates ddATP, ddCTP, ddGTP, and ddTTP.

* * * * *